United States Patent [19]

Gedeon

[11] Patent Number: 4,730,478
[45] Date of Patent: Mar. 15, 1988

[54] GAS ANALYZER

[75] Inventor: Andras Gedeon, Täby, Sweden

[73] Assignee: Icor AB, Bromma, Sweden

[21] Appl. No.: 875,344

[22] Filed: Jun. 17, 1986

[30] Foreign Application Priority Data

Jun. 18, 1985 [SE] Sweden ................................ 8503017

[51] Int. Cl.$^4$ ........................ G01N 27/00; H03L 1/02
[52] U.S. Cl. ........................................ 73/23; 331/156
[58] Field of Search ...................... 73/23, 27; 422/83;
324/65 R; 331/156

[56] References Cited

U.S. PATENT DOCUMENTS

| | | | |
|---|---|---|---|
| 3,164,004 | 1/1965 | King, Jr. ................................. | 73/23 |
| 3,260,104 | 7/1966 | King ....................................... | 73/23 |
| 3,322,981 | 5/1967 | Brenig ................................. | 310/8.9 |
| 3,879,992 | 4/1975 | Bartera ................................... | 73/23 |
| 3,948,081 | 4/1976 | Wessel et al. ........................... | 73/23 |
| 4,147,513 | 4/1979 | Bienkowski et al. ................... | 73/23 |
| 4,399,686 | 8/1983 | Kindlund et al. ...................... | 73/23 |
| 4,412,188 | 10/1983 | Helle et al. ........................... | 331/176 |
| 4,456,892 | 6/1984 | Vandergraaf ........................ | 331/176 |
| 4,462,246 | 7/1984 | Advani et al. ......................... | 73/23 |
| 4,572,900 | 2/1986 | Wohltjen ............................... | 73/23 |

FOREIGN PATENT DOCUMENTS

| | | | |
|---|---|---|---|
| 157247 | 10/1985 | European Pat. Off. ............... | 73/23 |
| 2165948 | 4/1986 | United Kingdom ................... | 73/23 |

Primary Examiner—Stewart J. Levy
Assistant Examiner—Hezron E. Williams
Attorney, Agent, or Firm—Lahive & Cockfield

[57] ABSTRACT

Apparatus for determining the proportion of a given gas component in a gas mixture, comprising a piezoelectric crystal provided with a surface layer containing a substance capable of selectively and reversibly adsorbing said gas component, and being so arranged that the gas mixture can be brought into contact with said surface layer. The crystal is incorporated in an oscillator circuit which produces an output signal representing the oscillating frequency of the crystal, and therewith the proportion of the given gas component in the gas mixture. For compensating the temperature dependency of the surface-layer adsorption of the relevant gas component, a thermistor ($R_T$) is arranged to be influenced by the same temperature variations as the piezoelectric crystal. Further, the output signal (S) of the oscillator circuit is connected to the input of an amplifying circuit, which incorporates the thermistor ($R_T$) and is so constructed that the degree of amplification of the circuit is dependent on the resistance of the thermistor in a manner such that the output signal ($V_U$) deriving from the amplifying circuit is substantially independent of temperature variations of the surface layer of the piezoelectric crystal.

4 Claims, 2 Drawing Figures

GAS ANALYZER

BACKGROUND

The present invention relates to apparatus for determining the proportion of a given gas component in a gas mixture.

It is well known that when wishing to detect the presence of and/or determine the proportion of a given component of a gas mixture, there can be used an apparatus or device which incorporates a piezoelectric crystal, e.g. a quartz crystal, having provided on its surfaces a thin substrate layer comprising one or more substances capable of reversibly and selectively adsorbing the gas component of interest, i.e. the relevant gas component, from a gas mixture, the crystal being so arranged as to enable the gas mixture being assayed to be brought into contact with the substrate layer. The substrate layer therewith adsorbs molecules of the relevant gas component from the gas mixture to an extent contingent on the concentration of said component in the mixture and increases in mass in dependence hereon, which results in a decrease in the vibration frequency of the piezoelectric crystal. The vibration frequency of the crystal is normally determined by incorporating the crystal in an oscillator circuit constructed to produce an output signal representative of the oscillating frequency of the oscillator circuit, and therewith also of the crystal, in relation to a reference frequency. The reference frequency is normally the oscillating frequency to another, similar crystal, which lacks the aforedescribed substrate layer but which, in all other respects, is arranged identically with the crystal provided with said substrate layer. An output signal representing the frequency difference of the two crystals will therefore constitute a measurement of the quantity of the relevant component present in the assayed gas mixture. Apparatus of this kind are described for example, in U.S. Pat. Nos. 3 164 004 and 4 399 686. Substances suitable for use as a substrate layer for the selective and reversible adsorption of many different gaseous components of a gas mixture are also known to the art.

One problem with gas analyzing apparatus of this kind is that the ability of the substrate material to adsorb the relevant gas component from a gas mixture is highly dependent on the temperature of the substrate material, such that with an unchanged concentration of the relevant gas component in the gas mixture the quantity of the component adsorbed decreases with increasing substrate layer temperatures. The sensitivity of the gas analyzer is thus correspondingly temperature dependent, and decreases with increasing substrate temperatures. In conjunction with gas analyzers for assaying respiration gas mixtures in order to determine the constituent proportion of anaesthetic gases of the type halogenated hydrocarbon compounds, such as halothane, enflurane, methoxy flurane and iso-flurane, said substrate layer being composed, for example, of different types of silicon oils, it has been found that the aforesaid temperature dependency has a form which can be expressed by the equation $$S \sim T^{-5/2} e^{1/T} \tag{1}$$

where S is the above-mentioned output signal representing the difference frequency of the crystals, and T is the temperature (°K.) of the substrate layer. Within a temperature range of 20°–45° C., which is an appropriate temperature range with gas analyzers of this kind, the change in analyzer sensitivity as a result of variations in temperature is in the order of 150%.

It will be realized that the aforesaid temperature dependency must be eliminated in some way. One possibility is to maintain the piezoelectric crystal and its substrate layer at a constant temperature. This can be effected by either cooling or heating the crystal. Cooling of the crystal results in the condensation of water vapor on the crystal, which creates problems, at least when analysing respiration gas mixtures, and renders an accurate assay totally impossible. When heating the crystal it is necessary to use temperatures of up to 50° C., at least when applicable to the aforesaid analysis of respiration or breathing gas mixtures, which results in a marked reduction in the sensitivity of the analyzer and also in far more rapid deterioration of the properties of the substrate layer, therewith reducing the useful life-span of the crystal. Both of these methods for maintaining the crystal and substrate layer at a constant temperature also have a considerable power consumption which, among other things, renders the use of a battery-driven gas analyzer impossible. A further difficulty in conjunction with maintaining the crystal and the substrate layer at a constant temperature resides in the fact that the crystal has a very low thermal capacity, and hence its temperature accompanies variations in ambient temperature extremely rapidly, i.e. in practice variations in the temperature of the analysed gas mixture.

Consequently, the object of the present invention is to provide an apparatus of the kind mentioned in the introduction with which the problem associated with temperature-dependent sensitivity is eliminated or, in all events, greatly reduced, without needing to maintain the crystal and its substrate layer at a constant temperature.

SUMMARY OF THE INVENTION

The most direct method of solving the aforementioned problem would be to measure the prevailing temperature of the piezoelectric crystal and correcting the analyzer output signal is dependence thereof. However, since the temperature dependency is complex, as made evident by the above equation (1), such a direct method is complicated and requires the provision of complex electronic circuitry.

The present invention is based on the discovery of a much simpler method of compensating for the temperature-dependent adsorption of the substrate layer.

BRIEF DESCRIPTION OF THE DRAWINGS

The characteristic features of the apparatus according to the invention are set forth in the following claims, and the invention will now be described in more detail with reference to the accompanying drawing, in which

DETAILED DESCRIPTION OF THE INVENTION

Figure 1:
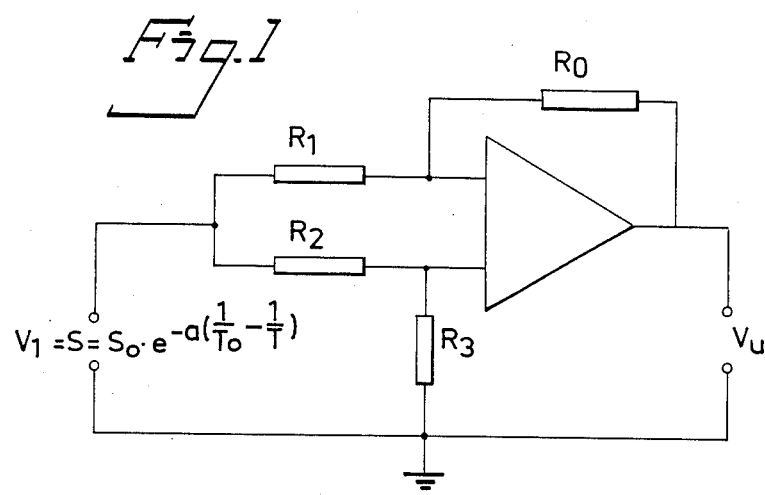
FIG. 1 is a circuit diagram illustrating schematically, and by way of example, an embodiment of the invention.

The fundamental principle of the invention resides in arranging a temperature-dependent electric component in a manner such that the component is subjected to the same temperature variations as the crystal and its substrate layer, and supplying the temperature-dependent output signal from the oscillator circuit incorporating the crystal to a signal processing circuit, preferably an amplifying circuit, in which the aforesaid temperature-dependent electric component is incorporated in a manner such that the signal processing circuit produces an output signal which is substantially compensated for the temperature-dependent variations in the adsorbing capacity of the substrate layer.

As mentioned in the aforegoing, the temperature-dependent output signal of the oscillator circuit can be expressed by the aforegoing equation (1). Within the temperature range of 15°-50° C. this equation can be very well approximated by the equation $$S = S_o \cdot e^{-a(\frac{1}{T_o} - \frac{1}{T})} \quad (2)$$

where $S_o$ is the output signal of the oscillator circuit at the temperature $T_o$ and a is a constant dependent on the properties of the substrate layer and the adsorbed gas component.

According to one preferred embodiment of the invention the temperature-dependent electric component used is a thermistor having a negative temperature coefficient (NTC), which is arranged so to be influenced by the temperature of the analysed gas in the same manner as the piezoelectric crystal provided with said substrate layer, and therewith subjected to the same variations in temperature as said layer. The circuit used for processing the output signal of the oscillator circuit is advantageously an amplifying circuit of the construction illustrated in FIG. 1, the output signal S of the oscillator circuit being applied to the input of said amplifying circuit.

The amplifying circuit includes an operational amplifier F which has a resistance feedback path through a resistor $R_o$, from its output to one of its inputs. The output signal S from the gas-analyzer oscillator circuit applied to the input of the amplifying circuit is connected to the feedback input of the operational amplifier F through a resistor $R_1$, and to the other input of the operational amplifier F via a resistive voltge divider comprising the resistors $R_2$ and $R_3$. If the resistance values of the resistors $R_o$, $R_1$, $R_2$ and $R_3$ are selected so that $$R_o >> R_1 \text{ and } R_2 >> R_3$$

the amplifying factor $V_U/V_I$ of the amplifying circuit can be expressed approximatively as $$\frac{V_U}{V_I} \approx -\frac{R_o}{R_1} \quad (3)$$

This gives $$V_U \approx -V_I \frac{R_o}{R_1} = -S_o \frac{R_o}{R_1} \cdot e^{-a(\frac{1}{T_o} - \frac{1}{T})} \quad (4)$$

According to a first embodiment of the invention the thermistor is coupled in the amplifying circuit in a manner to constitute the resistor $R_1$, i.e.

$$R_1 = R_T$$

where $R_T$ is the resistance of the thermistor.

Since the temperature-dependent resistance $R_T$ of the thermistor can be expressed as $$R_T = R_{T_o} \cdot e^{-b(\frac{1}{T_o} - \frac{1}{T})}$$

where $R_{T_o}$ is the resistance at the temperature $T_o$ and b is the characteristic temperature (°K.) of the thermistor, there is obtained $$V_u \approx -S_o \frac{R_o}{R_{T_o}} \cdot e^{(b-a)(\frac{1}{T_o} - \frac{1}{T})} \quad (5)$$

It will be seen from this expression that when the thermistor is selected so that $$a = b$$

the output signal $V_U$ of the amplifying circuit will be independent of the prevailing temperature T of the piezoelectric crystal and the substrate layer, i.e. independent of any variations of temperature in the crystal and its substrate layer, and proportional to the signal $S_o$, i.e. the output signal of the oscillator circuit at a given temperature, this output signal being representative of the proportion of the relevant gas component in the gas mixture influencing the substrate layer.

Comparison tests are being carried out with a gas analyzer of the aforedescribed kind of assaying the proportion of the anaesthetic gas isoflurane in a respiration gas mixture, the substrate layer containing a silicon oil. The temperature-dependency of the sensitivity of the gas analyzer was determined firstly without endeavouring to compensate for temperature and secondly with a temperature compensating circuit of the aforedescribed kind illustrated in FIG. 1. In this case, the resistance values of the amplifying circuit were $R_T=50K\Omega$ at 25° C., $R_o=1M\Omega$, $R_2=100K\Omega$ and $R_3=5K\Omega$, and the characteristic temperature of the thermistor was b=3934° K. In the graph of FIG. 2 the curve A represents the sensitivity K of the analyzer in respect of the narcotic as in question as a function of the temperature T (°C.) in the absence of temperature compensation, whereas the curve B represents the sensitivity of the analyzer as a function of temperature when using the aforedescribed temperature compensating circuit illustrated in FIG. 1. As will be seen, the temperature dependency was reduced to about one tenth when using the temperature compensating circuit.

Figure 2:
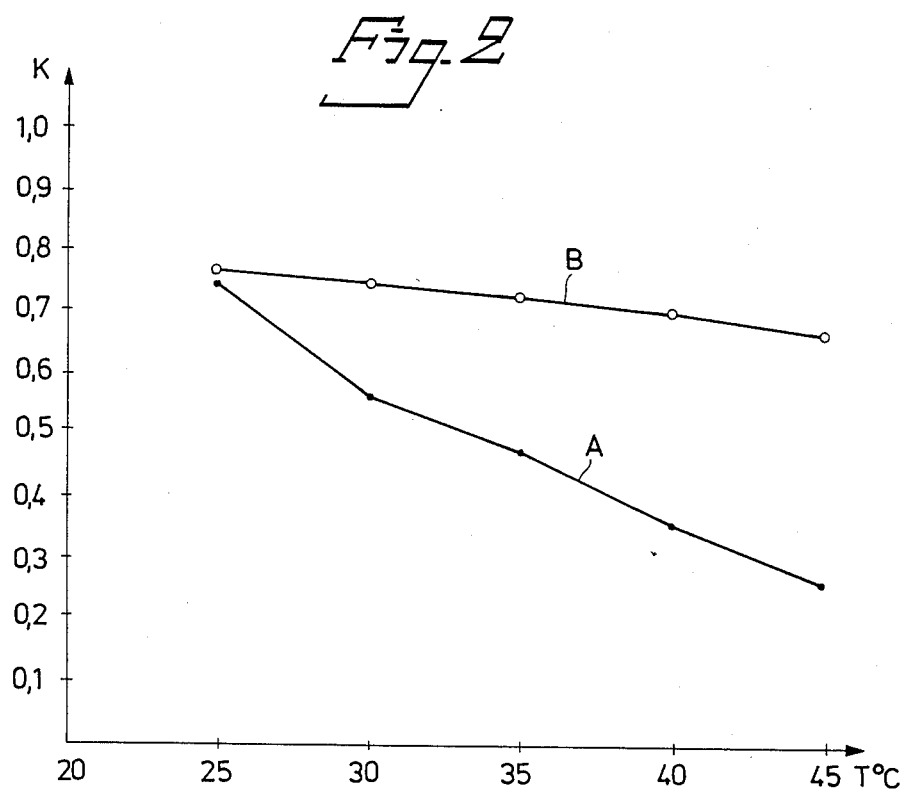
FIG. 2 is a graph illustrating the result obtained with a test apparatus constructed in accordance with the invention.

According to another embodiment of the invention, the temperature compensation sought for can also be achieved with the amplifying circuit illustrated in FIG. 1 by coupling the thermistor to form the resistor $R_3$, i.e.

$$R_3 = R_T \quad (7)$$

In this case, the resistance values of the resistor are selected so that $$R_o >> R_1 \text{ and } R_3 >> R_2$$

and simultaneously $$R_o \cdot R_2 >> R_1 \cdot R_3.$$

When the mutual resistance values of the resistors are selected in this way, the amplifying factor $V_U/V_I$ of the amplifying circuit can be expressed approximately as $$\frac{V_u}{V_I} \approx - \frac{R_2 \cdot R_o}{R_1 \cdot R_3} \quad (8)$$

which when applying expressions (2), (5) and (7) gives $$V_u \approx - \frac{R_2 R_o}{R_1 \cdot R_{T_o}} \cdot S_o \cdot e^{(b-a)(\frac{1}{T_o} - \frac{1}{T})} \quad (9)$$

The output signal $V_u$ will also in this case be substantially independent of the prevailing temperature T of the piezoelectric crystal and the substrate layer, when the thermistor is chosen so that a=b.

What is claimed is:

1. Apparatus for determining the proportion of a given gas component in a gas mixture, comprising:
    a piezoelectric crystal having a surface layer adapted to contact a gas, said surface layer containing a substance capable of reversibly adsorbing said component from a gas mixture;
    an oscillator circuit incorporating said crystal for producing an output signal representing the oscillating frequency of the crystal, said frequency corresponding to the proportion of said gas component in the gas mixture;
    a temperature-dependent thermistor adapted to be subjected to the same temperature variations as the surface layer of the crystal;
    a signal processing amplifying circuit to which said oscillator circuit output signal is applied and in which said thermistor is incorporated such that said amplifying circuit produces an output which substantially compensates for temperature-dependent variations of the adsorbing properties of said substance, said amplifying circuit having a degree of amplification dependent on the value of thermistor;
    said amplifying circuit signal further having a resistance feedback path to the one input of the amplifier through a feedback resistance, the output signal of the oscillator circuit being connected to said one input of the operational amplifier through the thermistor and to the other input to the operational amplifier by way of a resistive voltage divider, said feedback resistance being greater than the resistance of the thermistor, and said resistive voltage divider being dimensioned such that the part of the output signal of the oscillator circuit applied to said other input of the operational amplifier constitutes a small part of the total signal.

2. The apparatus of claim 1 wherein the thermistor has a negative temperature coefficient.

3. Apparatus for determining the proportion of a given gas component in a gas mixture, comprising:
    a piezoelectric crystal having a surface layer adapted to contact a gas, said surface layer containing a substance capable of reversibly adsorbing said component from a gas mixture;
    an oscillator circuit incorporating said crystal for producing an output signal representing the oscillating frequency of the crystal, said frequency corresponding to the proportion of said gas component in the gas mixture;
    a temperature-dependent thermistor adapted to be subjected to the same temperature variations as the surface layer of the crystal;
    a signal processing amplifying circuit to which said oscillator circuit output signal is applied and in which said thermistor is incorporated such that said amplifying circuit produces an output which substantially compensates for temperature-dependent variations of the adsorbing properties of said substance, said amplifying circuit having a degree of amplification dependent on the value of thermistor;
    said amplifying circuit further having an output signal which has a feedback path to the one input of the amplifier by way of a first resistance, the output signal of the oscillator circuit being connected to one input by way of a second resistance and to the other input of the operational amplifier by way of a voltage divider, which comprises a third resistance in series with said thermistor arranged such that the part of the output signal of the oscillator circuit connected to said other input of the operational amplifier is the part lying across the thermistor, said feedback resistance being much greater than said second resistance, the thermistor resistance being greater than the third resistance and, at the same time, the product of the negative resistance and the third resistance being greater than the product of the second resistance and the resistance of the thermistor.

4. The apparatus of claim 3 wherein the thermistor has a negative temperature coefficient.

* * * * *